US006482906B1

(12) United States Patent
Tocchetto Pires et al.

(10) Patent No.: US 6,482,906 B1
(45) Date of Patent: Nov. 19, 2002

(54) PROCESS FOR PREPARING AND USING NEODYMIUM NEODECANOATE

(75) Inventors: Neusa Maria Tocchetto Pires; Luiz Fernando Nicolini, both of Rio de Janeiro; Clóvis Henriques De Lira, Niterói; Carlos Roberto De Albuquerque Campos, Jaboatão dos Guararapes; Paulo Luiz De Andrade Coutinho, Rio de Janeiro, all of (BR)

(73) Assignee: Petroflex Industria E Comércio (BR)

( * ) Notice: Subject to any disclaimer, the term of this patent is extended or adjusted under 35 U.S.C. 154(b) by 0 days.

(21) Appl. No.: 09/571,157

(22) Filed: May 16, 2000

(30) Foreign Application Priority Data

May 27, 1999 (BR) .............................. 9902609

(51) Int. Cl.[7] .................................................. C08F 4/44
(52) U.S. Cl. ........................ 526/164; 526/335; 526/159; 502/263
(58) Field of Search ............................... 526/335, 159, 526/164; 502/263

(56) References Cited

U.S. PATENT DOCUMENTS 5,017,539 A * 5/1991 Jenkins et al. ............... 502/102
6,111,082 A * 8/2000 Yunlu et al. .................. 534/16

* cited by examiner

*Primary Examiner*—David W. Wu
*Assistant Examiner*—Ling-Siu Choi
(74) *Attorney, Agent, or Firm*—Jones, Tullar & Cooper, P.C.

(57) ABSTRACT

A new process for the preparation of neodymium neodecanoate, which is utilized as the metallic component, in a new process for the preparation of three-component homogeneous catalytic systems. The invention also deals with a solution polymerization process for the preparation of polybutadiene with a high content of the 1,4-cis units.

15 Claims, No Drawings

PROCESS FOR PREPARING AND USING NEODYMIUM NEODECANOATE

FIELD OF THE INVENTION

The present application refers to a process for the preparation of neodymium neodecanoate, to the process for the preparation of a homogeneous coordination catalytic system composed of three components, of which the metal compound is the neodymium neodecanoate, to the process for the solution polymerization of butadiene for the preparation of polybutadiene with a high content of the 1,4-cis isomer, and to the elastomeric products manufactured from this polymer, particularly tires for the automotive industry.

BACKGROUND OF THE INVENTION

During the last years, saving energy and protecting the environment have become priorities of society. The market requires more and more low fuel consumption vehicles and rubber components of higher durability and wear resistance. These requirements may be satisfied through the use of tires with low resistance to rolling and higher resistance to abrasion.

Products derived from butadiene are being largely produced on an industrial scale, especially polybutadiene with a high content of the 1,4-cis form, which exhibits excellent properties for application in the manufacture of tires for the automotive industry, like abrasion resistance, fatigue resistance, tear resistance, low heat build-up and low rolling resistance.

Physical and mechanical properties of polybutadienes, as well as their ease of processing, depend on the microstructure and the microstructure displayed by these polymers. Thus, molecular weight, molecular weight distribution, polydispersion, branching index, and cis content are the major responsible factors for the performance of these polymers.

The microstructure of polybutadienes, especially the content of 1,4-cis units, influences significantly the physical properties of the pure gum and the vulcanized products. However, they do not vary significantly in the range between 25 and 80 percent of the 1,4-cis units, but change rapidly beyond these limits. This is because polybutadienes have the capacity to crystalize under pressure, improving the physical properties of the polymer. This effect increases as the content of 1,4-cis units is raised. Thus intensive research is being carried out to develop new catalytic systems that are able to produce polymers with high stereospecificity by polymerization of conjugated dienes.

Great advances have been achieved, not only in the invention of new catalytic systems, but also in the development of new polymerization processes, that yield products with controlled molecular weight, distribution of molecular weight, branch content and microstructure.

Polybutadiene may be produced by different polymerization mechanisms. However, only the coordination catalysts make it possible to achieve a high degree of chemical and steric selectivity during the polymerization process.

Polybutadiene with a high content of 1,4-cis units may be prepared using stereospecific catalysts of the Ziegler-Natta type, based on organometallic complexes of transition metals. The commercially available technologies for the manufacture of this elastomer utilize solution processes and organometallic complexes based on cobalt, titanium, nickel, and rare earths.

The production systems of high cis polybutadiene based on titanium, cobalt, and nickel have some drawbacks. Firstly, it is necessary to use aromatic solvents, because these solvents favor the rate of polymerization, the yields, the cis content, and the molecular weight. However, aromatic solvents are more toxic, and generally more expensive than aliphatic solvents. Secondly, it is necessary to work at low polymerization temperatures in order to favor the formation of the 1,4-cis isomer. This requires sophisticated cooling systems of high investment cost. Thirdly, the conversion yields are below 90%, which entails a loss of productivity and an increase of investment and operational costs, since an additional stage for recovery of non-reacted monomer becomes necessary.

With relation to the polymer's properties, products resulting from technologies based on nickel, titanium, and cobalt exhibit mechanical properties that are inferior to the ones presented by polymers obtained via rare earths, especially properties such as tear resistance, fatigue resistance, abrasion resistance and heat build up. The polymers obtained from the use of rare earths show better processability, especially tack, green strength, and mill banding.

The European patent EP 406,920 mentions the use of catalytic systems containing metallic components of the rare earths series in the preparation of rubbers with excellent qualities.

The American U.S. Pat. No. 4,461,883, describes ternary catalytic systems consisting of $NdCl_3$ (neodymium chloride), an alcohol and triethylaluminum, which present serious disadvantages during industrial application. This is because $NdCl_3$ is solid and insoluble in an inert hydrocarbon, and the product of the reaction between the $NdCl_3$ and the alcohol is a precipitate that is insoluble in a hydrocarbon solvent, thus generating heterogeneous systems. Heterogeneous systems lead to wider polymer polydispersion, difficult control of molecular weight, and difficult reproducibility, when compared to homogeneous systems.

The Brazilian patent application PI 7804950 describes the use of monovalent and monodented chelates of rare earth metals and the American U.S. Pat. No. 3,297,667, the use of rare earth metals chelates with monovalent bidented or bivalent bidented binders in the catalytic systems. The American U.S. Pat. No. 4,242,232 states that chelate catalysts are solid substances that do not dissolve either in the monomer or in the solvents that are appropriate for polymerization processes. The products obtained by polymerization with these catalysts in the presence of organic solvents have the appearance of swollen agglomerates. The patent also discloses known catalysts consisting of (1) a rare earth salt of a carboxylic acid, (b) a trialkylaluminum, and (c) a Lewis acid, but that rare earth carboxylates are only slightly soluble in hydrocarbons and form highly viscous masses with them, even at high dilutions. However, the reaction of carboxylates with trialkylaluminum, according to the disclosure of the aforementioned patent, has solved the problem of their solubility.

The American U.S. Pat. No. 4,242,232 refers to the catalyst, to its preparation procedure, and to its application to the solution polymerization of conjugated dienes. This catalytic system differs from the one described in the prior art by the use of Lewis acids. The Lewis acids utilized are the organometallic halides of metals pertaining to the groups IIIA or IVA of the Periodic Table, and the halides of elements of the groups IIIA, IVA, and VA of the Periodic Table. The order of addition of the catalytic components is indifferent, and the reaction proceeds over a wide temperature range, which is generally limited by the boiling point of the solvent used. Polymerization occurs at temperatures that vary from 0° to 120° C.

The American U.S. Pat. No. 4,461,883 declares that the product of the reaction between the neodymium carboxylate and the trialkylaluminum is difficult to handle, since it is extremely sensitive to the presence of humidity and oxygen, which cause the deactivation of part of the catalyst, lowering the yield of polymerization. The U.S. Pat. No. 4,461,883 refers to the process for the production of polymers of conjugated dienes utilizing a catalytic system containing a soluble lanthanide carboxylate, obtained by reaction of the carboxylate with a Lewis base. The Lewis bases utilized are, for example, acetylacetone, tetrahydrofuran, pyridine, monohydric and dihydric alcohols, containing from 1 to 10 carbon atoms. The catalytic system contains, besides the metallic component, an organic compound of aluminum and an alkylaluminum halide. In the preparation process of the catalyst, the compound with the lanthanide series metal is made to react initially with the Lewis base, at temperatures from −50° to 150° C., and, subsequently, the reaction product is reacted with the other components, at temperatures that vary from −30° to 100° C. Polymerization can occur in the presence or absence of solvents. The polymerization temperature varies from −30° to 120° C.

The European patent EP 11,184 describes a catalytic system for the solution polymerization of conjugated dienes, which system comprises (a) a rare earth carboxylate, with the general formula $M(R_1 R_2 R_3 C O_3)_3$, in which the alkyl radicals $R_1$, $R_2$ and $R_3$ are the same or different ones, containing from 1 to 10 carbon atoms, the summation of all carbon atoms in the alkyl radicals being between 6 and 20, (b) a trialkyaluminm, and/or a halogenated hydride of alkylaluminum, and (c) a Lewis acid. The Lewis acids utilized are the organometallic halides of metals pertaining to the groups IIIA or IVA of the Periodic Table and the halides of the elements of the groups IIIA, IVA and VA of the Periodic Table.

In the majority of the above-mentioned references, the catalytic system contains, besides the compound of a rare earth metal, a trialkylaluminum or a dialkylaluminum hydride, and a halogenated ion in the form of Lewis acid.

The Brazilian patent PI 8205374 describes a catalytic system in which the Lewis acid was replaced by a halogenated organic derivative, which is more stable and, consequently, easier to handle, and promotes polymerization at temperatures that are not critical, even in case of bulk operation. The catalytic system may be preformed or prepared in situ. In both cases, its preparation may be carried out in presence or absence of hydrocarbon solvents. The order of addition of the catalyst components is not important. The preparation temperature is room temperature. The polymerization temperature is not critical, and varies from 0° to 200° C. The polymers of conjugated diolefins that are produced have a high content of the 1,4-cis units, with controlled molecular weight and a linear structure. The molar ratio of the organic halogenated derivative to the metal compound is equal to or greater than 0.33, being preferably between 0.5 and 3.0, and of the aluminum compound to the metal compound is greater than 20, preferably between 30 and 200.

The Brazilian patent PI 8301824 also deals with catalytic system based on the use of metallic compounds of rare earths, but with four components, for the polymerization of conjugated diolefins. The system comprises at least one compound of a metal of the group IIIB of the Periodic Table, at least one organic compound of an alkylaluminum or its monohydride derivative, at least a compound containing one or more hydroxyls and, sometimes, at least one organic compound containing chlorine or bromine in ionizable form, or at least one halogenated organic derivative. The patent states that polar compounds when present, far from acting as catalyst poisons, act as true catalytic components, to the point of making the presence of the halogenated organic component unnecessary. However, the preferred synergic action is provided by hydroxylated and halogenated components for the accomplishment of the invention, even when the amount of the halogenated components is very small. The main advantages of the invention are the elimination of the drying stage of the diluent, and/or of the monomer, and the high activity of the catalyst, in terms of consumption of the catalytic system per unit of weight of polymer. Water, when utilized as the component that contains hydroxyls, is only slightly soluble in the aliphatic hydrocarbons, but very soluble in the diolefins in liquid state, and may be introduced jointly with the monomer through the process for preparation of the catalyst in situ. The water may also be dispersed as droplets in the hydrocarbon medium, but, preferably, shall not be present jointly with the metal compound. The order in which the catalytic components are placed to react among themselves and with the monomer(s) is not predetermined. It is preferable that the catalyst be prepared at room temperature in concentrated solution, and then diluted with the monomer. The molar ratios between the aluminum compound and the metal containing component is greater than 20, preferably between 30 and 200, between the hydroxyls containing compound and the metal containing component is greater than 2, preferably between 4 and 100, and between the halogenated organic compound and the metal containing component is equal to or greater than zero, preferably between 0.2 and 3.0. Polymerization can occur in presence or absence of inert diluents. The polymerization temperature is not critical, and may be chosen between 0° and 200° C. The neodymium content in the polybutadiene may reach values lower than 20 ppm, depending on the reaction time.

The patent PI 8402579 refers to a process for the production of polybutadiene of the 1,4-cis type prepared by catalytic polymerization of butadiene monomer in the absence, or substantial absence, of solvents or diluents. The presence of diluent is generally defined as being about 2% by weight in relation to the quantity of butadiene monomer. The object of that patent is the development of an appropriate catalytic system to eliminate the difficulties faced by the industry in the polymerization in the absence, or substantial absence, of solvents or hydrocarbon diluents of low boiling point, that is, bulk polymerization. The catalytic system is prepared by bringing into contact the catalytic components in the hydrocarbon vehicle, at a temperature equal to or higher than room temperature. One of the accomplishments of the invention is the catalytic system that may be prepared by bringing the components into contact in the hydrocarbon vehicle, in the order indicated below, and at room temperature (20 to 25° C.):

neodymium alcoholate, phenolate, or carboxylate;
organometallic compound of aluminum or its hydride;
halogen compound; and
hydroxyl compound.

The relation between the number of hydroxyl and/or carboxyl groups and of neodymium atoms ranges from 2:1 to 100:1; between the number of aluminum and neodymium atoms ranges from 20:1 to 200:1; and between the halogen and neodymium atoms ranges from 0.2:1.0 to 3:1.

The patent PI 8402579 does not claim the process for preparation of the neodymium salt, but describes in Example 1 the process for the preparation of neodymium naphthenate, that is utilized in the preparation of the catalyst of the above-mentioned invention for the preparation of high-cis polybutadiene, which is prepared from a mixture of neodymium oxide, a carboxylic acid, which is the napthenic acid, an aqueous solution of hydrochloric acid, and hexane. The mixture is kept under agitation, in a nitrogen atmosphere, at a temperature of 60° C., for three hours. At the end of this period a turbid solution with an oily aspect is obtained.

The catalytic system is prepared by adding in reactor the neodymium salt solution, obtained directly from the process above, and the solution of diisobutylaluminum in hexane. The mass is kept under agitation, at room temperature, for one hour. At the end of this period, a solution of ethylaluminum dichloride is added, and agitation is maintained for an additional half an hour under an inert atmosphere, at room temperature. The catalytic solution is withdrawn from the vessel and mixed with anhydrous liquid butadiene.

Several catalytic systems for the polymerization of butadiene which are capable of producing polybutadiene with a high content of the 1,4-cis form are, therefore, known at the state-of-the-art. Literature teaches the existence of various technological routes for the preparation of these elastomers with the use of neodymium based coordination catalysts. In spite of solution polymerization being the most utilized process by the industry, the polymerization process most frequently discussed in the patent literature is bulk polymerization, which intends to eliminate the post-treatment states required by solution polymerization.

The prior art shows the development of a catalytic system for bulk polymerization that is able to eliminate the chain transfer reactions, that are responsible for the formation of low molecular weight polymers, and the secondary reactions of reticulation and cyclization in the polymer. The system shall present enough activity to keep a low level of catalytic residues in the polymer, as well as high activity and selectivity at the operating conditions. Additionally, the prior art attempts to solve the difficulties in engineering, rheology, and heat transfer inherent to the treatment of highly viscous masses.

However, solution polymerization continues to be the most convenient technological route for the commercial preparation of polybutadienes with a high content of the 1,4-cis isomer. Solution polymerization is carried out in presence of an organic solvent capable of dissolving the monomer, the polymer and the catalyst. This process offers the advantage of facilitating the heat exchange during the polymerization reaction, consequently controlling the polymerization reaction and the polymerization temperature for the production of linear polymers, soluble and gel-free, having controlled molecular weight and molecular weight distribution. The main operational difficulty to be met is the maintenance of the solids content at levels that make it easier to handle the polymeric mass. Due to the fact that the polymer is soluble in the utilized organic solvent, the viscosity of the solution tends to increase with increasing molecular weight of the polymer. During the polymerization period, the solution becomes too excessively viscous to be handled in conventional polymerization systems, unless the solids content is kept at a very low level. In the commercial polymerization processes it is desirable to obtain a polymerizing mass with a high polymer concentration consisting of a material that is easy to handle and does not adhere to the walls of the utilized reaction vessel.

SUMMARY OF THE INVENTION

The present invention discloses an improved solution polymerization process, either by a continuous or batch system, for the preparation of polybutadiene with a high content of 1,4-cis units, with molecular weight and molecular weight distribution adequate for the fabrication of elastomeric articles, especially tires for the automotive industry, by using a new catalytic system that specifically utilizes neodymium neodecanoate that is prepared in accordance with a new process also disclosed herein.

The first object of this application is to provide a process for the preparation of a neodymium compound that is the neodymium neodecanoate.

As mentioned in the literature, the presence of moisture in the polymerization catalysts inhibits the catalytic activity. The Brazilian patent PI 8301824 refers to catalytic systems with four components, in which one component is a hydroxylated compound, such as water. But said patent excludes the presence of water jointly with the metallic component present in the catalyst. It states as preferential description the introduction of water dispersed as droplets in the hydrocarbon medium. The present invention discloses a new process for the preparation of neodymium neodecanoate that takes place in a free manner without temperature control, in the presence of hydrochloric acid diluted to low concentrations, in which the quantity of synthesis water in the final product is not minimized, that is, the excess of water is eliminated solely by settling.

The second object of this invention is a process for the preparation of a new homogeneous coordination catalytic system with three components, the metal compound of which is neodymium neodecanoate prepared according to the new process of the invention. It was discovered that the application of these carboxylates with a considerable content of humidity, brought about a significant increase in the period of useful life of the catalytic system and in its activity, in the process for the preparation of polybutadiene with high content of the 1,4-cis units. The new preparation process for the catalytic system is characterized by the fact that it is conducted at temperatures well below room temperature, and by the critical order of addition of the components. Thus, catalysts which are highly active and stereospecific are obtained, yielding catalysts with increased useful lifetime.

The invention has still as its object the improved solution polymerization process that uses said catalytic system to prepare polybutadiene with high content of the 1,4-cis units, e.g., a 1,4-cis content higher than 97%, as well as the application of these polybutadienes to the fabrication of elastomeric products, especially tires for the automotive industry.

DETAILED DESCRIPTION

The process for preparation of neodymium neodecanoate, according to the invention, is characterized by the preparation of a sludge of neodymium oxide in an organic solvent, aliphatic, cycloaliphatic, or mixtures of these, at temperatures between room temperature and 100° C., and the reaction of that sludge with neodecanoic acid in the presence of hydrochloric acid diluted to low concentrations, in that same temperature range. At the end of the reaction the final product appears as a slightly turbid solution due to the presence of non-reacted neodymium oxide, and may have an oily aspect depending on the concentration of neodymium neodecanoate. Said solution may contain up to 40,000 ppm of synthesis water. Next, the neodymium salt solution is subjected to settling, from which the supernatant phase results in a clear solution (independently from the neodymium concentration), excess of acid and synthesis water in the range from 8,000 to 25,000 ppm, preferably from 13,000 to 20,000 ppm, more preferably from 15,000 to 20,000 ppm The supernatant solution thus obtained is separated, inertized with nitrogen and stored to be utilized later in the preparation of the catalyst.

The aliphatic and cycloaliphatic organic solvents utilized according to the invention are the hydrocarbon solvents, like hexane, heptane, cyclohexane, or mixtures of them wherein hexane is the preferred solvent.

The molar ratio between neodecanoic acid and neodymium oxide may range from 6:1 to 15:1, being preferably from 6:1 to 9:1.

The homogeneous catalytic system with three components of the invention is composed of the following reagents:

A) neodymium neodecanoate;
B) alkylaluminum or its hydride derivative, preferably diisobutylaluminum hydride;
C) organic halide, preferably t-butyl chloride.

The preparation process of the catalyst according to the invention proceeds by the reaction among the three catalytic components in organic solvents, aliphatic, cycloaliphatic, or mixture of these, but preferably hexane, following the addition order indicated by B+A+C, at temperatures between 0° and 18° C., preferably between 6° and 14° C. A solution of the alkylaluminum component in the treated solvents is prepared, cooled to temperatures between 0° and 18° C. To this solution the neodymium neodecanoate solution is added, with a known water content, e.g., with a moisture content higher than 13,000 ppm, prepared in accordance with the previously defined process. The mixture is maintained under agitation and cooling for at least 30 minutes. Next, the t-butyl chloride is added, pure or dissolved in the treated organic solvent. After the addition of chloride is finished, the mixture is allowed to react under agitation and cooling for at least 30 minutes. The catalyst is allowed to age for at least 30 minutes before being utilized. The molar ratios between components B and A lie between 5:1 and 50:1, preferably between 8:1 and 25:1. The molar ratios between components C and A lie between 0.2:1 and 4.5:1, preferably between 1.5:1 and 3.5:1.

The polymerization process of the invention is conducted in solution, either as a continuous or a batch process, in presence of an organic solvent, aliphatic, cycloaliphatic or a mixture of these. The preferred solvent according to the invention is hexane. The reaction may be conducted adiabatically or under controlled temperature. The reaction proceeds in the temperature range between room temperature and 150° C., preferably between 60° and 110° C. The catalyst concentration employed depends on the desired polymer properties, and may vary from 0.1 to 0.5 mols of neodymium per 100 kg of butadiene.

The process of the invention can still utilize chain modifiers known to the technique, of the alkylaluminum type, like triisobutylaluminum, diisobutylaluminum hydride, triethylaluminum, among others, in the molar relation aluminum:neodymium of 0–30:1, e.g., 0.1:1–30:1. The polymerization is ended by the addition of interruptors known to the technique, like water and alcohols. The polymer is stabilized by the addition of antioxidizers used conventionally in the technique.

The final product is recovered through thermal drying or mechanical coagulation followed by drying.

The polybutadiene with a high content of 1,4-cis units prepared according to the invention may be utilized for the manufacture of tires, belts, and other rubber articles, molded or extruded.

EXAMPLES

The following examples illustrate the different realizations of the invention.

Synthesis of the Neodymium Neodecanoate

The synthesis of neodymium neodecanoate prepared in accordance with the process described in the invention of the present application was conducted as per Examples 1 and 2 below. The neodecanoic acid used in the process of preparation of the neodymium neodecanoate was the "VERSATIC 10" commercialized by Shell Chemicals.

Example 1

In a glass flask with a capacity of 1.000 ml, provided with mechanical agitation, initially at the temperature of 24° C., were added 78.16 g of treated hexane, and 23.36 g of neodymium oxide with a purity equivalent to 99% by weight. After vigorous agitation of the mixture for complete homogenization, 2.0 ml of filming hydrochloric acid diluted in ten parts of water were added. Next, 78.47 g of commercial neodecanoic acid were added, triggering the reaction. After two hours of reaction, a turbid lilac solution was obtained. The solution was allowed to settle for the withdrawal of the non-reacted neodymium oxide and some excess of water, and after the settling presented itself as clear lilac solution, with a non-oily aspect, with 37.8% by weight of neodymiumneodecanoate and 13,805 ppm of water.

Example 2

In a glass flask with a capacity of 1,000 ml provided with mechanical agitation, initially at the temperature of 55° C., 78.16 g of treated hexane and 23.36 g of neodymium oxide with a purity equivalent to 99% by weight. After vigorous agitation of the mixture for complete homogenization, 2.0 ml of fuming hydrochloric acid diluted in ten parts of water were added. Next, 78.47 g of commercial neodecanoic acid were added, triggering the reaction. After one hour of reaction, a turbid lilac solution was obtained. The solution was allowed to settle for the withdrawal of the non-reacted neodymium oxide and some excess of water, and after the settling presented itself as clear lilac solution, with a non-oily aspect, with 45.9% by weight of neodymium neodecanoate and 17,834 ppm of water.

Synthesis of the Catalyst

The synthesis of the catalytic system according to the process described in the invention of the present application was conducted as per the description below.

The catalysts were synthesized in glass bottles with a capacity of 500 ml, dried in an oven at 120° C. for at least 12 hours. The bottles containing inside a magnetic stirrer were sealed when still hot, under pressure, with rubber gaskets and metallic caps, and later cooled down with dry nitrogen. The alkylaluminum compound was introduced into the bottles by means of syringes, and the bottles were cooled to the catalyst preparation temperature. After stabilization of the temperature, a solution of neodymium neodecanoate in dry hexane, prepared as described in Examples 1 and 2, was added to the content of the bottle. After 30 minutes of the addition of neodymium neodecanoate, the hexanic solution of t-butyl chloride as added to the reaction medium. The catalyst was allowed to age and utilized for the butadiene polymerization.

Examples 3 to 7

Refer to catalysts synthesized according to the preparation procedure described above. Samples of neodymium neodecanoate prepared previously in accordance with the process of the invention were especially synthesized and employed in the above-mentioned examples.

Example 8 is presented as a comparative example and refers to the use of a neodymium neodecanoate solution containing 250 ppm of water and not prepared in accordance with the process of the invention.

| Ex. n°. | Diisobutylaluminum hydride | | Neodymium neodecanoate | | t-butyl chloride | | Hexane | T | t |
|---|---|---|---|---|---|---|---|---|---|
| | g | mmols | g | mmols | g | mmols | g | °C. | hours |
| 3 | 14.979 | 105.328 | 3.969 | 6.039 | 1.414 | 15.285 | 96.980 | 5 | 48 |
| 4 | 7.842 | 55.146 | 3.749 | 5.704 | 1.674 | 18.094 | 57.765 | 10 | 191 |
| 5 | 8.159 | 57.378 | 3.622 | 5.509 | 1.592 | 17.208 | 65.043 | 8 | 338 |
| 6 | 3.656 | 25.708 | 1.423 | 2.166 | 0.644 | 6.966 | 21.319 | 5 | 14 |
| 7 | 3.819 | 26.854 | 1.502 | 2.285 | 0.234 | 2.525 | 22.731 | 12 | 23 |
| 8 | 6.229 | 43.799 | 2.795 | 4.253 | 1.124 | 12.154 | 36.331 | 5 | 25/48 |

T - preparation and aging temperature
t - aging time.

T—preparation and aging temperature
t—aging time.

Polymerization Process

Batchwise polymerization was conducted under an inert atmosphere of pure nitrogen in a Parr reactor of stainless steel with a capacity of 1 gallon. The solvent and the butadiene were dried previously, and the dried products had 6 ppm of water maximum The catalyst and the alkylaluminum, when it is utilized as molecular weight modifier, were introduced in the reactor by means of syringes. The addition order of the reaction components was: solvent, monomer, alkylahlminum, and catalyst. The reactions were initiated at different temperatures, and conducted adiabatically until their ends, for a determined period of time.

The reactions were ended with an excess of ethanol, and the polymers were stabilized with a system of non-staining antioxidizers, composed of trinonyl-phenyl-phosphite plus a blocked phenol. After homogenization for 20 minutes, the polymers were coagulated in hot water under vigorous mechanical agitation, and dried in an oven with forced air circulation, at 60° C. for 24 hours.

The polymers were characterized by using techniques of Proton Nuclear Magnetic Resonance and Gel Permeation Chromatography.

Examples 9 to 14 depict the polymerization process for the Preparation of polybutadiene following the procedure described above, employing the catalysts synthesized in Examples 3 to 8

Example 9

In the reactor were added 674.91 g of hexane, 410.871 g of an hexanic solution of butadiene at 34.4% by weight, and 3.91 g of the catalyst prepared in Example 3 allowed to age during 48 hours. The initial reaction temperature was 48° C., the total time of reaction, three hours, and the final conversion, 60.7%. The weighted average molecular weight was 416,157, and the cis content of the polymer equal to 98.6%.

Example 10

In the reactor were added 680.064 g of hexane, 408.150 g of an hexanic solution of butadiene at 34.4% by weight, and 6.55 g of the catalyst prepared in Example 4 allowed to age for 191 hours. The initial reaction temperature was 50° C., the total time of reaction, two hours, and the final conversion, 98.0%. The coagulated polymer presented Mooney viscosity equal to 64.5 ML(1+4), and a cis units content of 98.6%.

Example 11

To the same weights of hexane and butadiene utilized in the example above were added 2.562 g of an hexanic solution of diisobutylaluminum hydride at 17.16% by weight, as molecular weight modifier, and 3.07 of the catalyst prepared in Example 5, aged for 338 hours. The reaction initial temperature was 80° C. After one hour, the conversation was equivalent to 86.0%.

Example 12

In the reactor were added 736.868 g of hexane, 404.7 g of an hexanic solution of butadiene at 34.4% by weight, and 4.23 g of the catalyst prepared in Example 6 allowed to age for 14 hours at 5° C. The reaction was initiated at 70° C., and after two hours, the final conversion was 99.6%. The coagulated polymer presented Mooney viscosity equal to 48.8 ML(1+4), and a content of cis units of 98.0%.

Example 13

To the same weights of hexane and butadiene utilized in Example 10 above were added 3.727 g of the catalyst synthesized in Example 7, aged for 23 hours. The initial reaction temperature was 78° C. The conversion reached 61.4% after two hours of reaction. The final polymer, coagulated and dried, presented Mooney viscosity equal to 26.4 ML(1+4), and 96.0% of cis units.

Examples 14 and 15
(Comparative)

In the reactor were added 736.868 g of hexane, 404.7 g of an hexanic solution of butadiene at 34.4% by weight, and 3.467 g and 3.477 g (respectively in Examples 14 and 15) of the catalyst prepared in Example 8.

For comparative purposes, two polymerizations were conducted, the first with the catalyst aged for 25 hours, and the second with the same catalyst after 48 hours of aging. For the same conditions of reaction and conversion, the resulting polymer of the reaction with the catalyst aged for 48 hours presented a Mooney viscosity 12 points higher than the viscosity of the product obtained with the catalyst aged for 25 hours, showing a partial deactivation of the catalyst in less than 24 hours.

Variations

Many variations of the above will be obvious to those skilled in the art. Thus, the invention is defined by the claims.

What is claimed is:

1. A process for the preparation of neodymium neodecanoate for use as the metallic component of a coordination catalyst, comprising the steps of:
    a) preparing of a sludge of neodymium oxide in an organic solvent selected from the group consisting of aliphatic solvent, cycloaliphatic solvent, and a mixture of these, at temperatures between room temperature and 100° C.;
    b) reacting this sludge of neodymium oxide with neodecanoic acid in the presence of hydrochloric acid diluted to a catalytically effective amount up to 2.0 parts in volume of fuming hydrochloric acid in 10 parts in volume of water, at the same temperature range, the mole ratio of the neodecanoic acid and the neodymium oxide ranging from 6:1 to 15:1, to produce a final reaction product which is a solution slightly turbid with or without an oily aspect, which contains up to 40,000 ppm of synthesis water;
    c) settling the product resulting from the above reaction to obtain a supernatant phase which is a clear solution containing an excess of acid and about 8,000 to 25,000 ppm of synthesis water;
    d) separating the supernatant phase to form a solution of neodymium neodecanoate, maintaining it under nitrogen, and storing it for later utilization in catalyst preparation.

2. The process according to claim 1, wherein preparation of the sludge of neodymium oxide is accomplished using hexane as the organic solvent.

3. The process according to claim 1, wherein the supernatant phase contains an excess of acid and 13,000 to 25,000 ppm of synthesis water.

4. The process according to claim 1, wherein the supernatant phase contains an excess of acid and 15,000 to 25,000 ppm of synthesis water.

5. The process according to claim 1, wherein the mole ratio of the neodecanoic acid and the neodymium oxide ranges from 6:1 to 9:1.

6. The process according to claim 1, wherein preparation of the sludge of neodymium oxide is accomplished without temperature controls.

7. A process for the preparation of homogeneous coordination catalyst system which consists of the reaction product of A) neodymium neodecanoate; B) an alkylaluminum or its hydride derivative; and C) an organic halide, the said process comprising the steps of:
    a) preparing an alkylaluminum or its hydride solution in an organic solvent selected from the group consisting of aliphatic solvent, cycloaliphatic solvent and a mixture of these;
    b) cooling the solution described in a) to a temperature between 0° and 18° C.;
    c) adding a solution of neodymium neodecanoate, obtained according to the process defined in claim 1;
    d) keeping the solution under agitation and cooling to a temperature between 0° C. and 18° C. for at least 30 minutes;
    e) adding the organic halide pure or in solution in an organic solvent selected from the group consisting of aliphatic solvent, cycloaliphatic solvent and a mixture of these to form a mixture;
    f) reacting the mixture under agitation and cooling to a temperature between 0° C. and 18° C. for at least 30 minutes to form a catalyst;
    g) aging the catalyst for at least 30 minutes prior to use.

8. The process according to claim 7, wherein the alkylaluminum prepared is diisobutylaluminum hydride.

9. The process according to claim 7, wherein the organic halide is t-butyl chloride.

10. The process according to claim 7, wherein the organic solvent for preparing the alkylaluminum or its hydride solution is hexane.

11. The process according to claim 7, wherein a mole ratio between the alkylaluminum or its hydride and neodymium neodecanoate is between 5:1 and 50:1.

12. The process according to claim 7, wherein a mole ratio between the alkylaluminum or its hydride and neodymium neodecanoate is between 8:1 and 5425:1.

13. The process according to claim 7, wherein a mole ratio between the organic halide and the neodymium neodecanoate is between 0.2:1 and 4.5:1.

14. The process according to claim 7, wheein a mole ratio between the organic halide and the neodymium neodecanoate is between 1.5:1 and 3.5:1.

15. A process for solution polymerization preparation of polybutadiene with a high content of 1,4-cis units, comprising contacting butadiene with an aged catalyst system that is prepared according to the following steps:
    a) preparing an alkylaluminum or its hydride solution in an organic solvent selected from the group consisting of aliphatic solvent, cycloaliphatic solvent and a mixture of these;
    b) cooling the solution described in a) to a temperature between 0° C. and 18° C.;
    c) adding the solution of neodymium neodecanoate, obtained according to the process defined in claim 1;
    d) keeping the solution under agitation and cooling to a temperature between 0° C. and 18° C. for at least 30 minutes,
    e) adding an organic halide pure or in solution in an organic solvent selected from the group consisting of aliphatic solvent, cycloaliphatic solvent and a mixture of these to form a mixture;
    f) reacting the mixture under agitation and cooling to a temperature between 0° C. and 18° C. for at least 30 minutes to form a catalyst; and
    g) aging the catalyst for at lest 30 minutes to form said aged catalyst system.

* * * * *

UNITED STATES PATENT AND TRADEMARK OFFICE
CERTIFICATE OF CORRECTION

PATENT NO.    : 6,482,906 B1
DATED         : November 19, 2002
INVENTOR(S)   : Pires et al.

It is certified that error appears in the above-identified patent and that said Letters Patent is hereby corrected as shown below:

Column 10,
Line 32, change "conversation" to -- conversion --.

Column 11,
Lines 19 and 42-43, change "mole ratio" to -- molar ratio --.

Column 12,
Lines 21, 24, 27 and 30, change "mole ratio" to -- molar ratio --.
Line 26, change "5424:1" to -- 25:1 --.

Signed and Sealed this

Eighteenth Day of March, 2003

JAMES E. ROGAN
*Director of the United States Patent and Trademark Office*